United States Patent
Clerc et al.

(10) Patent No.: US 6,551,352 B2
(45) Date of Patent: Apr. 22, 2003

(54) METHOD FOR ATTACHING AXIAL FILAMENTS TO A SELF EXPANDING STENT

(75) Inventors: Claude O. Clerc, Flemington, NJ (US); James T. Hogan, Lausanne (CH); Carol A. Kaufmann, Philadelphia, PA (US); E. Skott Greenhalgh, Wyndmoor, PA (US)

(73) Assignee: Bionx Implants, Inc., Blue Bell, PA (US)

( * ) Notice: Subject to any disclaimer, the term of this patent is extended or adjusted under 35 U.S.C. 154(b) by 0 days.

(21) Appl. No.: 09/847,919

(22) Filed: May 3, 2001

(65) Prior Publication Data

US 2002/0165597 A1 Nov. 7, 2002

(51) Int. Cl.⁷ .................................................. A61F 2/06
(52) U.S. Cl. ....................... 623/1.2; 623/1.5; 623/1.51; 623/1.53; 623/1.22; 156/143
(58) Field of Search ................................ 623/1.49, 1.5, 623/1.51, 1.53, 1.54, 1.22, 1.17, 1.2, 1.38, 1.34; 427/2.1–2.31; 622/1.34; 156/143

(56) References Cited

U.S. PATENT DOCUMENTS

| | | | |
|---|---|---|---|
| 4,655,771 A | 4/1987 | Wallsten | 623/1 |
| 4,954,126 A | 9/1990 | Wallsten | 600/36 |
| 4,955,899 A | 9/1990 | Della Corna et al. | 623/1 |
| 5,192,308 A | 3/1993 | Ostapchenko | 623/1 |
| 5,254,113 A * | 10/1993 | Wilk | 606/8 |
| 5,382,259 A | 1/1995 | Phelps et al. | 606/151 |
| 5,383,925 A | 1/1995 | Schmitt | 623/1 |
| 5,582,619 A | 12/1996 | Ken | 606/191 |
| 5,628,788 A | 5/1997 | Pinchuk | 623/1 |
| 5,700,286 A | 12/1997 | Tartaglia et al. | 623/1 |
| 5,728,131 A | 3/1998 | Frantzen et al. | 606/194 |
| 5,741,332 A * | 4/1998 | Schmitt | 623/1.53 |
| 5,758,562 A | 6/1998 | Thompson | 87/33 |
| 5,833,705 A | 11/1998 | Ken et al. | 606/191 |
| 5,853,418 A | 12/1998 | Ken et al. | 606/191 |
| 5,876,448 A * | 3/1999 | Thompson et al. | 623/1.15 |
| 5,957,974 A | 9/1999 | Thompson et al. | 623/1 |
| 6,004,388 A | 12/1999 | Ken et al. | 606/191 |
| 6,013,084 A | 1/2000 | Ken et al. | 606/191 |
| 6,015,432 A | 1/2000 | Rakos et al. | 623/1 |
| 6,042,605 A | 3/2000 | Martin et al. | 623/1 |
| 6,165,210 A | 12/2000 | Lau et al. | 623/1.12 |
| 6,340,367 B1 * | 1/2002 | Stinson et al. | 623/1.34 |
| 6,342,068 B1 * | 1/2002 | Thompson | 623/1.53 |
| 6,357,104 B1 * | 3/2002 | Myers | 29/527.1 |
| 6,364,904 B1 | 4/2002 | Smith | 623/1.22 |

* cited by examiner

Primary Examiner—David H. Willse
Assistant Examiner—Suzette J. Jackson
(74) Attorney, Agent, or Firm—Synnestvedt & Lechner LLP

(57) ABSTRACT

Methods for attaching an axial filament to the body of a self expanding stent, the filament serving to enhance the radial self expanding force of the stent body. Also stents having enhanced radial self expansion characteristics.

39 Claims, 5 Drawing Sheets

METHOD FOR ATTACHING AXIAL FILAMENTS TO A SELF EXPANDING STENT

FIELD OF THE INVENTION

The invention pertains to self-expanding stents and particularly to methods of attaching axial filaments to the stent body to increase its radial expansion force.

BACKGROUND OF THE INVENTION

Self-expanding stents such as braided or knitted stents for surgical implantation in body lumens (tubular vessels) are known for repairing or strengthening the vessels. A stent essentially is a hollow tube that supplements the body vessel. With respect to the medical condition of stenosis, in which a body lumen tends to collapse or otherwise close, the stent supports the wall of the vessel to prevent it from collapsing or closing. A blood vessel that is narrowed due to the build up of intra-vascular plaque is one example of a stenosis. With respect to the medical condition of aneurism, in which a body lumen is weakened and cannot properly withstand the internal pressure within the vessel and bulges out or ruptures, the stent serves essentially the opposite function in that it substitutes for or supplements a weakened portion of the vessel. Stents are known for insertion in blood vessels, bile ducts, colons, trachea, bronchi, esophagi, urethra, ureters, etc.

Many different types of stents are commercially available at this time. Most stents need to be radially constricted, i.e., reduced in diameter, so that they can be inserted into the body lumen. Once they are in situ, the stent can be radially expanded to the desired diameter. Stents are known that are fabricated from rigid, but deformable materials that, when bent by force, tend to retain the bent shape. Such stents may be inserted into the body lumen in an unstressed radially minimal shape while mounted over a deflated balloon. When the stent is in situ, the balloon is inflated in order to radially expand the stent, which will then retain the radially expanded shape after the balloon is deflated and removed.

Another type of stent is termed a self-expanding stent. Self-expanding stents can be compressed radially, but will expand to their original shape once the radially constricting force is removed. Some types of self-expanding stent are formed from materials that are superelastic or have shape memory characteristics. Such stents are commonly made of Nitinol, a biocompatible alloy that, depending on its chemical composition and thermomechanical history, may be used either as a shape memory material or a superelastic material. The Ultraflex stent manufactured and sold by Boston Scientific Corporation is an example of a knitted Nitinol stent.

Another type of self-expanding stent that reverts to its original shape because it undergoes only elastic deformation when radially compressed is exemplified in U.S. Pat. No. 1,205,743, issued to Didcott and incorporated herein by reference. Didcott discloses a self-expanding, braided surgical dilator stent particularly adapted for esophageal dilation, but which can be adapted for use in other body vessels. This patent discloses a stent generally in accordance with the stent 10 shown in FIG. 1A hereof. It comprises a hollow tubular member, the wall of which is formed of a series of individual, flexible, thread elements 12 and 14, each of which extends helically around the central longitudinal axis of the stent. A first subset of the flexible thread elements 12 have the same direction of winding and are displaced relative to each other about the cylindrical surface of the stent. They cross a second plurality of helical thread elements 14 which are also displaced relative to each other about the cylindrical surface of the stent, but having the opposite direction of winding. Accordingly, as shown in FIG. 1A, the threads 12 of the first subset cross the threads 14 of the second subset at crossing points 16. FIG. 1A illustrates an embodiment in which the crossing threads are fully interlaced, however, the crossing threads may be interlaced at other intervals, e.g., every other crossing point or every third crossing point.

As the stent is axially stretched, i.e., as the longitudinal ends 18 and 20 are forced away from each other, the diameter reduces, as shown in FIG. 1B. Likewise, if the wall of the stent is constricted so as to reduce the stent's diameter, the stent elongates. In other words, radial constriction and axial elongation go hand in hand. When the force is released, the stent tends to spring back to its resting diameter and length. The force with which the stent returns to its original state depends on many factors, including the rigidity of the individual threads, the number of threads, and the original (resting) crossing angle, $\alpha$, of the threads. The rigidity of the threads, in turn, depends upon such factors as the material out of which they are fabricated and the thickness of the threads. In general, the greater the rigidity and/or the greater the resting crossing angle a of the threads, the greater the radial expansion force. The relationships between the stent deformation and mechanical properties as a function of its geometry and material properties is described in Jedwab and Clerc, "A Study of the Geometrical and Mechanical Properties of a Self-Expanding Stent—Theory and Experiment", Journal of Applied Biomaterials, Vol. 4, pp. 77–85 (1993).

The desired radial expansion force for a given stent depends on the application. When used in blood vessels, stents are commonly used to treat stenoses. Accordingly, such applications require relatively high radial expansion forces. Other applications, such as esophageal applications, require much lower forces.

U.S. Pat. No. 4,655,771 issued to Wallsten discloses a stent of the Didcott design particularly adapted for transluminal implantation in blood vessels for treating stenosis and aneurisms.

In some applications, such as the esophageal application particularly discussed in the aforementioned patent to Didcott, the stent is temporary. In other applications, such as the blood vessel application discussed in the aforementioned Wallsten patent, the stent is permanent. In permanent installations, the tissue of the body lumen within which the stent is placed tends to grow around the stent such that the stent essentially becomes incorporated with the tissue of the body vessel and thus becomes permanently affixed. However, in the weeks or months before this occurs, the stent is held in position by friction between the outer surface of the stent body and the inner surface of the vessel created by the radial expansion force of the stent. Thus, the resting diameter of the stent is selected to be slightly larger than the inner diameter of the vessel so that there is a constant force between the inner wall of the vessel and the outer wall of the stent.

Bioabsorbable stents are also known in the prior art. Bioabsorbable stents are manufactured from materials that dissolve over an extended period of time when exposed to body fluids and are absorbed into the surrounding cells of the body.

Various bioabsorbable materials that are suitable for fabricating stents are known in the prior art including polymers such as poly-L,D-lactic acid, poly-L-lactic acid, poly-D- lactic acid, polyglycolic acid, polylactic acid, polycaprolactone, polydioxanone, poly(lactic acid-ethylene oxide) copolymers, or combinations thereof. Vainionp at al., Prog Polym. Sci., vol. 14, pp. 697–716 (1989); U.S. Pat. Nos. 4,700,704, 4,653,497, 4,649,921, 4,599,945, 4,532, 928, 4,605,730, 4,441,496, and 4,435,590, all of which are incorporated herein by reference, disclose various compounds from which bioabsorbable stents can be fabricated.

Self-expanding braided stents rely on the spring force of the crossing threads that form the stent body to provide the radial expansion force. The magnitude of the radial expansion force is, therefore, a function of such factors as the number of threads, the size of the individual threads, the moduli of elasticity and rigidity of the thread material, and the initial crossing angle of the threads. Self-expanding knitted stents rely on a separate set of factors, including size and number of threads employed, the flexibility of the individual threads, and the particular knit pattern.

These characteristics of the stent, however, must be chosen based on factors in addition to the desired radial expansion force. For instance, the size of the threads is at least partially limited by the size of the lumen within which it will be employed. Further, characteristics of the material forming the stent body and thus the tensile strength and moduli of elasticity and rigidity of the material is limited to materials which can be safely placed in a human body.

Stents made from bioabsorbable materials exhibit different properties than corresponding metallic stent designs. Examples of properties that must be controlled when using bioabsorbable materials include degradation rates, material creep, and material position memory. These factors also affect the radial expansion force of the stent.

Accordingly, it is desirable to have some other or additional means by which to enhance the radial self expansion force of the stent.

It is an object of the present invention to provide methods and designs to achieve optimum performance employing polymeric materials in stents and more preferably polymeric bioabsorbable materials.

It is another object of the present invention to provide an improved method of attaching to a polymeric stent supplemental elastomeric filaments for increasing the radial expansion force of the stent.

It is further object of the present invention to provide an improved bioabsorbable stent with enhanced radial self expansion force.

It is yet a further object of the present invention to provide an improved bioabsorbable stent with attached supplemental elastomeric filaments for increasing the radial expansion force of the stent.

SUMMARY OF THE INVENTION

The invention pertains to methods for attaching to a stent an axial elastomeric filament for enhancing radial expansion force of a self expanding stent, particularly a polymeric, braided, self expanding, stent. It also pertains to stents having attached axial filaments for enhancing the radial expansion force of the stent. In accordance with the invention, the axial filament or filaments are adhesively bonded to the stent body either over their entire length or at intervals. In one embodiment, adhesive is applied with a syringe or a glue gun over the length of the filament. The stent, including the filaments, is then heat treated to cause the glue to bond the filaments to the stent body. Alternately, the glue may be applied only at those points where the axial filament intersects with a thread forming the body of the stent. In another embodiment, the glue is applied to a free standing filament and the filament is subsequently incorporated in or laid on the stent body.

In another embodiment, the entire stent with the axial filament is sprayed with adhesive. In yet a further embodiment of the invention, a portion or all of the stent, including the filaments, is dipped into an adhesive solution.

In another embodiment in which the axial filaments are interwoven with the threads forming the stent body, there is no adhesive and the friction force between the filament and the threads is sufficient to keep the axial filaments in place.

In yet a further embodiment of the invention, a band of adhesive is applied to the stent body with a syringe or glue gun and the adhesive itself forms an axial filament.

In one other embodiment of the invention, the stent is dipped in an elastomer solution. The elastomer is then heat cured. In this embodiment, the elastomer bonds to the threads that form the actual body of the stent. The threads with the elastomer coating are stiffer than the threads without the elastomer coating. Accordingly, the tendency of the stent body to return to the radially expanded position in which it was cured is increased. Any portion of the stent body up to and including the entire stent can be dipped in the elastomer in accordance with this embodiment.

In yet another embodiment, the stent can be held in a radially expanded position when the stent is sprayed or dipped into the elastomer solution and/or during the subsequent heat curing step. After the elastomer is heat cured, the stent will have a larger resting radial diameter than it otherwise would have had.

DETAILED DESCRIPTION OF THE INVENTION

As previously noted, the diameter of a self-expanding stent can be reduced and the length commensurately increased by applying either a radially restrictive force or a longitudinally lengthening force. When that force is removed, the stent tends to spring back towards its original diameter and length. Also as previously noted, the magnitude of the radially expansive force depends on many factors, including the material and particularly the rigidity of the threads, the thickness of the threads, the number of threads, and the crossing angle at rest of the threads. Generally, the greater the crossing angle at rest, the greater the radially expansive force. The magnitude of the expansive force is important for several reasons. For instance, the expansive force applied against the inner walls of the body vessel within which the stent is installed is the force that holds the stent in place until the tissue of the vessel can grow over and around the stent and thus permanently affix the stent within the vessel. Further, in many applications, the very purpose of the stent is to hold the vessel open and thus the proper magnitude of radially expansive force is critical. In some applications, such as implantation in blood vessels, the expansive force needs to be relatively large to hold the vessel open. In others, such as esophageal applications, the force must be considerably less.

In many applications, it may be desirable to supplement the radially expansive force inherently provided by this type of stent design. For instance, the size of the vessel and/or the route through which the stent must be inserted may dictate that the threads be thin or of a certain number that is insufficient to provide the desired radially expansive force.

U.S. patent application Ser. No. 09/626,638 filed Oct. 4, 2000, entitled SELF-EXPANDING STENT WITH ENHANCED RADIAL EXPANSION, assigned to the same assignee as the present invention and fully incorporated herein by reference, discloses several different mechanisms for enhancing the radial expansion force of a bioabsorbable, braided, self-expanding stent. One of the mechanisms disclosed therein for enhancing radial expansion force utilizes one or more axial filaments that are attached to the stent body.

Figure 1A:
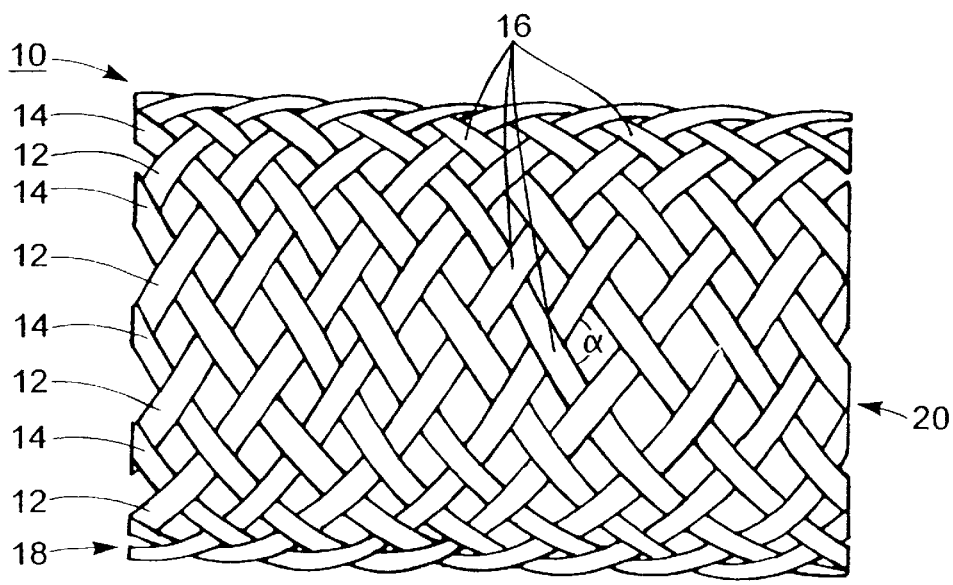
FIG. 1A is a plan view of a braided, self expanding stent in accordance with the prior art in its rest position.
Figure 1B:
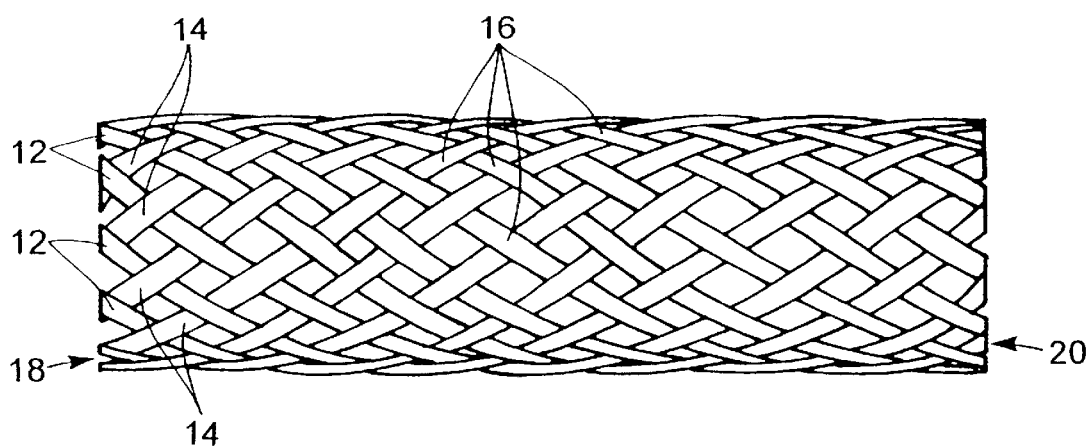
FIG. 1B is a plan view of the stent of FIG. 1A shown in a radially constricted/axially elongated state.
Figure 2:
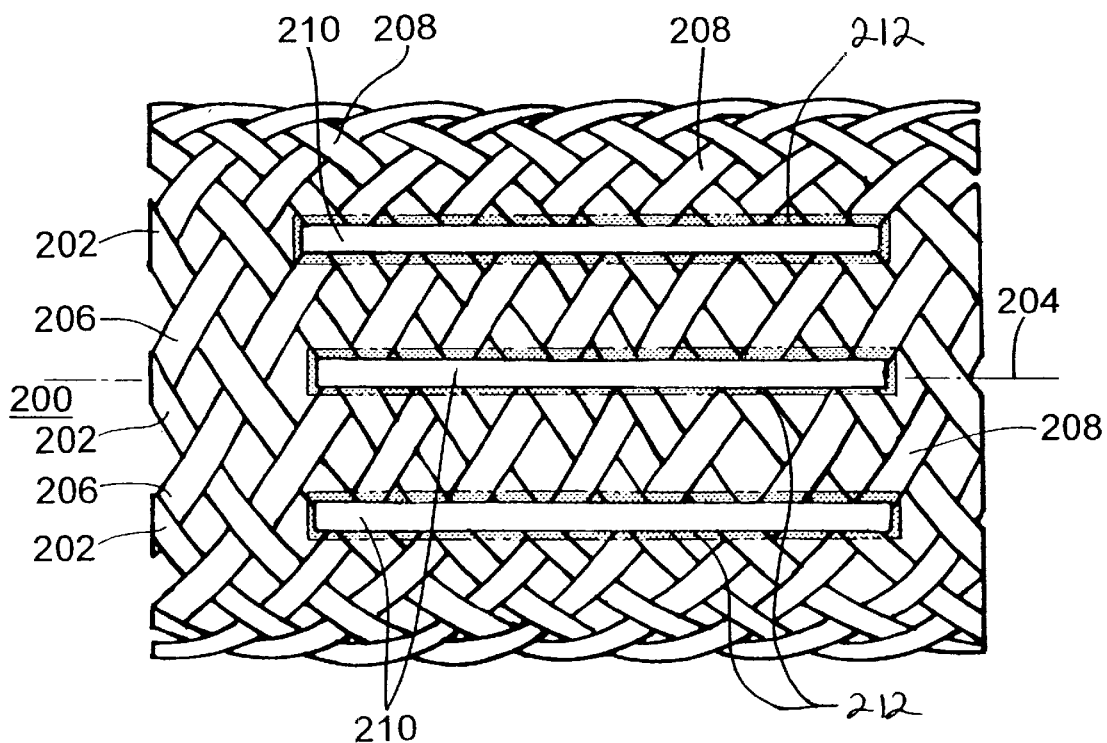
FIG. 2 is a plan view of a braided self, expanding stent in accordance with a first embodiment of the present invention.

FIG. 2 is a plan view of a stent 200 in accordance with the aforementioned patent application and further illustrating a first embodiment of the present invention. FIG. 2 illustrates a braided self-expanding stent 200. However, it should be understood that the methods and apparatus in accordance with the present invention also can be applied to any kind of self-expanding stent. Further, while the invention will be described herein with respect to particular embodiments wherein at least the threads forming the stent body are formed of a bioabsorbable material, it should be understood by persons of skill in these arts that the invention also can be applied in connection with non-bioabsorbable stents. The body of the stent of FIG. 2 is constructed primarily in accordance with the prior art and is composed of a first set of threads 202 helically wound around the longitudinal axis 204 of the stent 200 and a second plurality of threads 206 helically wound in the opposite direction around the longitudinal axis 204 of the stent. The first and second sets of threads 202 and 206 cross each other at crossing points 208 and have crossing angles at rest of α. The two sets of threads may or may not be braided with each other. The two sets of threads may or may not be joined at the crossing points 208.

The threads 202 and 206 forming the stent body can be made of any suitable material, including various plastics, metals, clothes, polymers and/or bioabsorbable and bioresorbable materials. In this specification, the term bioabsorbable is used to refer to both bioabsorbable materials and bioresorbable materials to the extent that some groups of persons working in the relevant fields may make a distinction between the two terms.

Incorporated into the stent are axial filaments 210 that run along the body of the stent and enhance the radial expansion force of the stent.

The axial filaments 210 preferably are elastic i.e., they recover their shape after being stretched. The axial filaments tend to counteract any axially elongating force and/or apply an axially constrictive force to the stent body. Accordingly, since axial constriction and radial expansion go hand in hand, the axial filaments enhance the radial expansion force of the stent.

Alternately or additionally, the axial filaments 210 can be fabricated of a material that shrinks in length when exposed to moisture or body temperature. The shrinkage of the axial filaments 210 will apply a longitudinally constricting and, therefore, radially expanding, force on the stent. The elastic axial filaments may be attached to the stent body such that they are in a state of non expansion when the stent is at its rest diameter (i.e., the diameter when no axial or radial force is applied to the stent body). In this type of embodiment, the axial filaments would counteract radially constricting forces or axially elongating forces applied to the stent and thus tend to enhance the radial expansion force up to the point where the stent diameter reaches its rest position. However, the axial filaments would have no tendency to increase the diameter of the stent beyond its rest diameter.

In other embodiments, the axial filaments are attached to the stent body such that they are in an elongated state when the stent would otherwise be at its rest diameter. In this type of embodiment, the axial filaments, not only counteract radially constricting forces or axially elongating forces applied to the stent, but also enhance the radial expansion force beyond the point where the stent diameter reaches what would otherwise be its rest diameter. Accordingly, in any given application, the axial filaments will cause the stent to have a larger diameter than it would have otherwise.

This last described embodiment can be produced either by holding the stent in an axially constricted/radially expanded position during affixation of the axial filaments, or by holding the axial filaments in an elongated state during affixation, or both.

Usually, during insertion, the entire stent, including the axial filaments, are longitudinally stretched in order to reduce its diameter so that it can be inserted into a body lumen more easily. When the stent is released from the insertion apparatus, the stent, under its own force as well as the supplemental force applied by the axial filaments, provides radially expansive force against the walls of the vessel within which it is inserted.

Suitable materials for the axial filaments are biostable or preferably bioabsorbable elastic polymers that are biocompatible. The biostable elastomers consist mainly of polyurethane and silicone elastomers. One of the first elastomeric fibers produced was elastane or spandex, a segmented polyurethane, that was later commercialized by DuPont under the trade name Lycra™. Spandex is also available from other manufacturers such as Globe Manufacturing Corp. Several other companies manufacture biostable polyurethane elastomers especially for medical applications and medical implants. Thermedics Inc., a division of Thermo Electron Corp., manufactures several grades of biostable polyurethane elastomers commercialized under the trade names Tecoflex™, Tecothane™, Carbothane™, Tecophilic™ and Tecoplast™. Elastomedic Pty Ltd. has a family of biostable polyurethane elastomers commercialized under the trade name Elast-Eon™. Cardiotech International, Inc. has a family of biostable polyurethane elastomers commercialized under the trade names Chronoflex™ and Chronothane™. Cardiotech International, Inc. also commercialized Chronoprene, a thermoplastic rubber elastomer that can be used to manufacture axial filaments in accordance with the present invention.

The Polymer Technology Group Incorporated has a family of biostable polyurethane elastomers commercialized under the trade names Biospan®, Bionate®, Elasthane®, Carbosil®, and Pursil®. Some of these polyurethanes contain silicone as soft segments.

Those skilled in the art are aware that polyurethanes are susceptible to hydrolitic chain scission and, therefore, the term biostable may actually indicate very slow degradation kinetics.

Silicones are another family of suitable elastomers for the axial filaments. Nusil Technology manufactures several grades of medical silicone elastomers. Applied Silicone Corporation, a division of Rhodia, commercialized other suitable silicone elastomers under the trade name Silbione®.

Preferably, however, the axial filaments are made out a bioabsorbable elastomer. Epsilon polycaprolactone, available, for instance, from Birmingham Polymers, Inc., is a suitable bioabsorbable elastomer. Polyactive, available from Isotis, is another suitable bioabsorbable elastomer.

U.S. Pat. Nos. 5,468,253, and 5,713,920, assigned to Ethicon Inc., describe a suitable bioabsorbable elastomer that is a copolymer of epsilon-caprolactone, trimethylene carbonate, glycolide and para-dioxanone. U.S. Pat. No. 5,113,624, also assigned to Ethicon, Inc., describes a suitable bioabsorbable elastomer that is a copolymer of lactide and p-dioxanone.

Suitable medical grade biodegradable polyurethane have also been synthesized. For instance, "Structure-Property Relationships of Degradable Polyurethane Elastomers containing an Amino Acid-Based Chain Extender" by Skarja and Woodhouse, J. Of Applied Polymer Science, Vol. 75, pp. 1522–1534 (2000), describes such biodegradable polyurethane elastomers.

Tepha, Inc., a subsidiary of Metabolix, Inc., is developing various grades of PHA (polyhdroxyalkanoate), a biocompatible and bioabsorbable polymer. The properties of these polymers range from stiff for PHB(polyhydroxybotyvate) to rubbery elastomers such as PHO (polhydroxyoctanoate).

By incorporating bioabsorbable axial filaments into a bioabsorbable stent, the entire device can be made bioabsorbable. However, it is not necessary that the entire stent be bioabsorbable. Typically it is most important for a stent to have a particular radial expansion force for a brief period of time immediately after it is installed, before the tissue at the implantation site grows around the stent. Particularly, as a stent remains in place, the surrounding tissue will grow over it and incorporate the stent into the tissue. However, immediately after the stent is in installed, it is held in place essentially exclusively by the friction created by the radial expansion force of the stent body against the inner wall of the lumen. Therefore, it may be advantageous in many cases for the axial filaments to be bioabsorbable and the stent body to be non-bioabsorbable. In this manner, the enhanced radial expansion force is applied only for a limited period immediately after the stent is installed. Then, as the axial filaments degrade over time, the enhanced radial force also diminishes over time. In fact, even where the entire stent is bioabsorbable, including the main body and the axial filaments, it is possible to fabricate the axial filaments so that they degrade more quickly than the stent body, thus providing decreasing radial expansion force over time in a fully bioabsorbable stent.

Alternately, the stent body can be bioabsorbable while the axial filaments are not. In such a case, the axial filaments will simply be incorporated into the tissue as the tissue grows around the stent. Accordingly, the axial filaments will not interfere with flow through the body lumen once the stent disintegrates.

It has been found that attaching the axial filaments to the stent body by means of an adhesive is most effective. The adhesive used to attach the axial filaments to the stent body also should meet certain criteria. It should be medical-grade biocompatible. Most of the aforementioned axial filament materials can be dissolved in a solvent and used as the adhesive. If the stent, including the stent body and the axial filaments, are bioabsorbable, then it may also be preferable for the adhesive to be bioabsorbable.

Once the axial filament is in place on the stent body, the solvent can be evaporated thus leaving behind the elastomer acting as an adhesive between the axial filaments and the body of the stent. Silicone also has been found to be a particularly suitable adhesive.

FIG. 2 illustrates a particular embodiment of the invention in which the axial filaments are attached to the stent body by adhesive 212. First, the axial filaments are brought into contact with the stent body. In the particular embodiment illustrated in FIG. 2, the axial filaments are laid on top of the outer surface of the stent body. However, the filaments alternately could be laid on the inside surface of the body or interwoven into the helically wound fibers 202 and 206. Next, a suitable adhesive in liquid form dissolved in solvent is applied over the entire length of the axial filaments by syringe or glue gun. The stent is then heat treated to evaporate the solvent within which the adhesive is dissolved. After the solvent has evaporated, the axial filaments are adhered to the stent body.

Alternately, the adhesive solution may be applied in lines over the stent body by syringe or glue gun and the axial filaments then laid on or in the adhesive bands. The stent, including the adhesive and axial filaments is then heat treated as previously discussed to form a structure similar to that shown in FIG. 2. In this particular embodiment, the adhesive solution should be sufficiently viscous so that it can form bands on the stent body even though the adhesive bands must traverse open spaces between threads.

Figure 3:
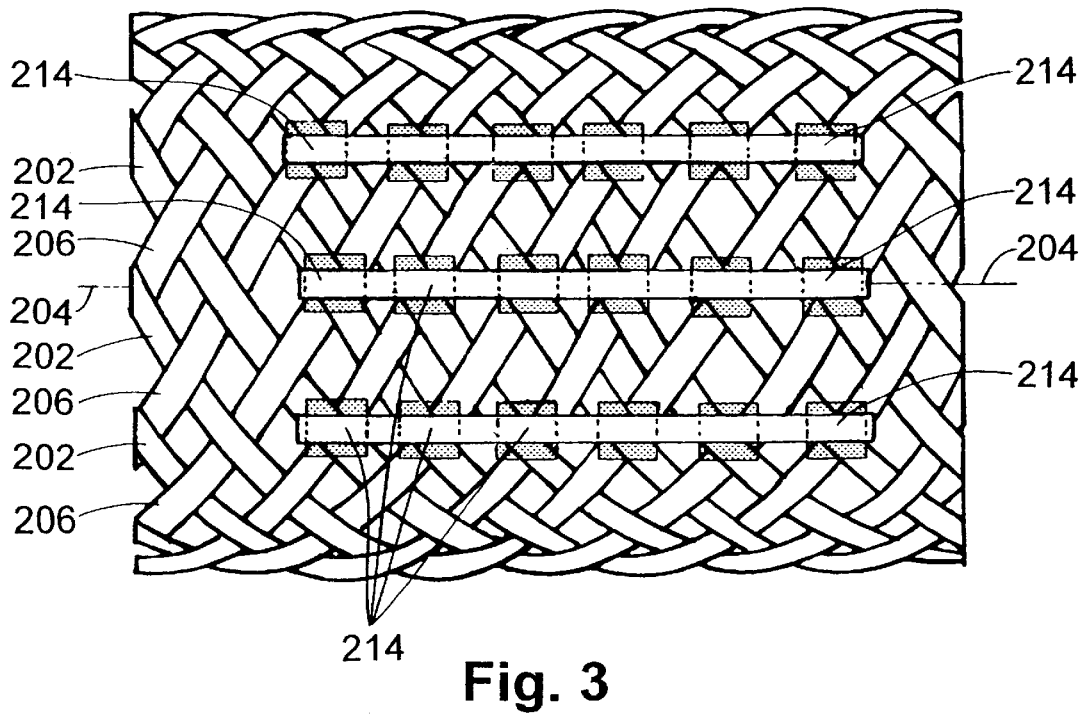
FIG. 3 is a plan view of a braided, self expanding stent in accordance with a second embodiment of the present invention.

FIG. 3 illustrates an alternate embodiment which is similar to the embodiments discussed above in connection with FIG. 2, except that the adhesive is applied only at the points 214 where the axial filament overlie the threads 202, 206 that form the stent body. However, as was the case discussed above in connection with the FIG. 2 embodiment, the filaments alternately can be bonded to the outer surface or the inner surface of the stent body.

In a preferred embodiment of the invention, the axial filament is interwoven with the braided structure of the stent body at the time of the braiding of the stent body. However, in alternate embodiments, the axial filaments could be laid on the inside surface, outside surface or both of the stent body after the stent body is braided. Even further, the axial filaments could be woven into the stent structure as shown in FIG. 3, but at a time after the stent body itself has been fully formed.

In another embodiment of the invention, the axial filaments can first be covered with the adhesive and then applied to the stent body. The adhesive-covered axial filaments can be applied on the outer surface of the stent body, the inner surface of the stent body, both surfaces and/or interwoven with the threads of the stent body. Then, the stent, including the axial filaments can be heat treated as discussed above in connection with FIGS. 2 and 3.

Figure 4:
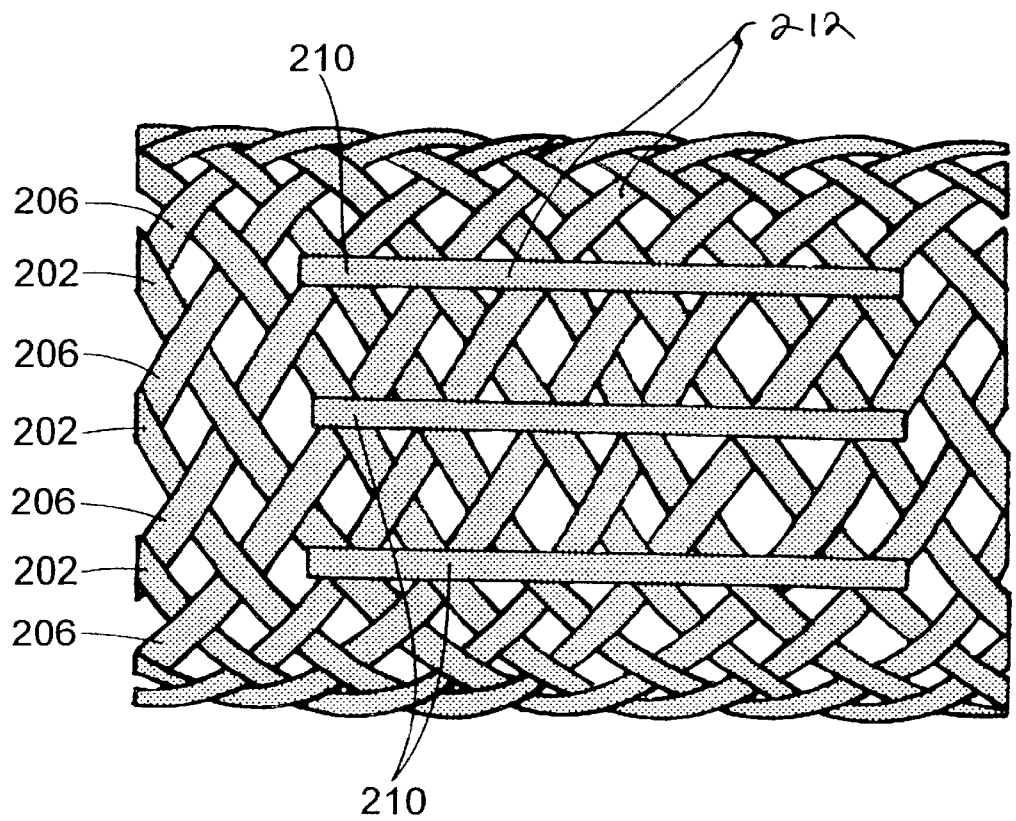
FIG. 4 is a plan view of a braided, self expanding stent in accordance with a third embodiment of the present invention.

In yet another embodiment of the invention illustrated in FIG. 4, the axial filaments 210 can be applied on the outer surface of the stent body (shown), the inner surface of the stent body and/or interwoven with the threads of the stent body and the entire stent sprayed with the adhesive solution. The stent is then heat treated as discussed above. As can be seen, in this embodiment, the entire stent 200 including the stent body and the axial filaments 210 are coated with the adhesive 212. In another embodiment of the invention, the stent can be prepared exactly in the manner discussed above in connection with FIG. 4 except that, instead of spraying the stent body with an adhesive solution, the stent body is dipped in an adhesive solution.

With particular respect to the last two embodiments discussed above, (in which all of the helical threads of the stent body as well as the axial filaments are coated with adhesive), the adhesive layer on the threads of the stent body will alter the stiffness of the stent. Particularly, it will increase the stiffness of the stent. Thus, inherently, it also will increase the resistance of the stent to changes in radial diameter or axial length. Accordingly, the adhesive itself helps enhance the radial self expansion force of the stent.

Figure 5:
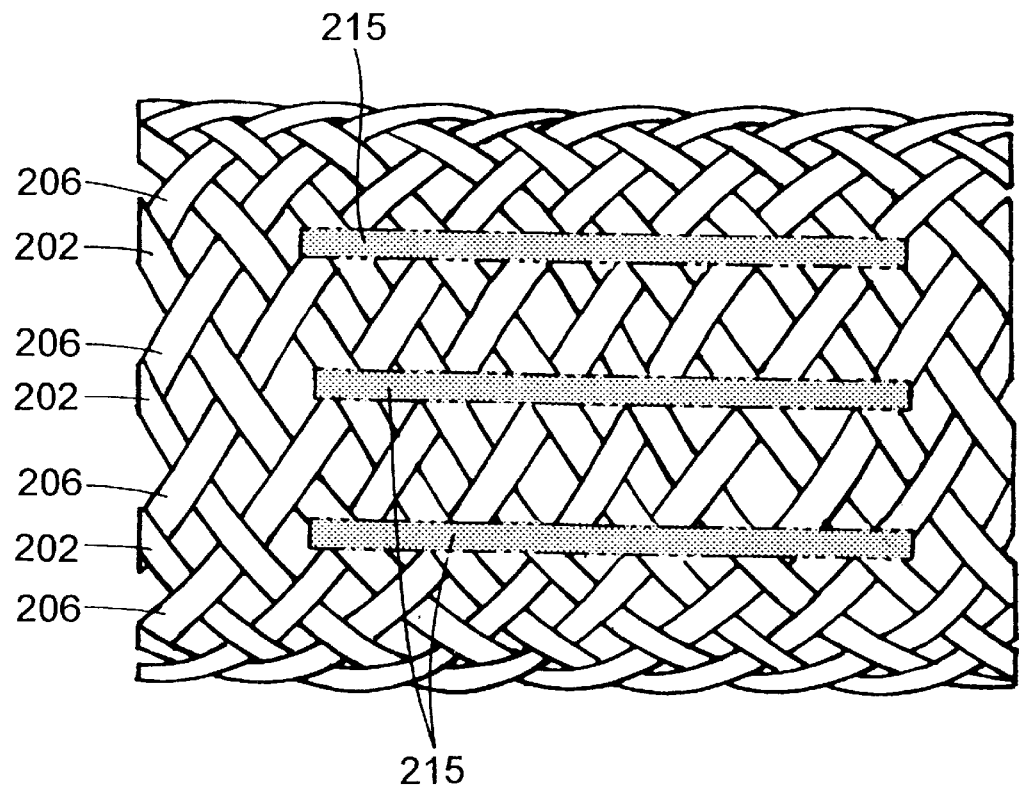
FIG. 5 is a plan view of a braided, self expanding stent in accordance with a fourth embodiment of the present invention.

In another embodiment illustrated in FIG. 5, instead of axial filaments, axial bands of adhesive 215 are applied directly to the stent body. The quantity of adhesive (e.g., the thickness of the adhesive bands) is sufficient to enhance the radial expansion force of the stent in and of themselves, without the need for axial filaments. The axial bands of adhesive can be continuous or discontinuous.

Figure 6:
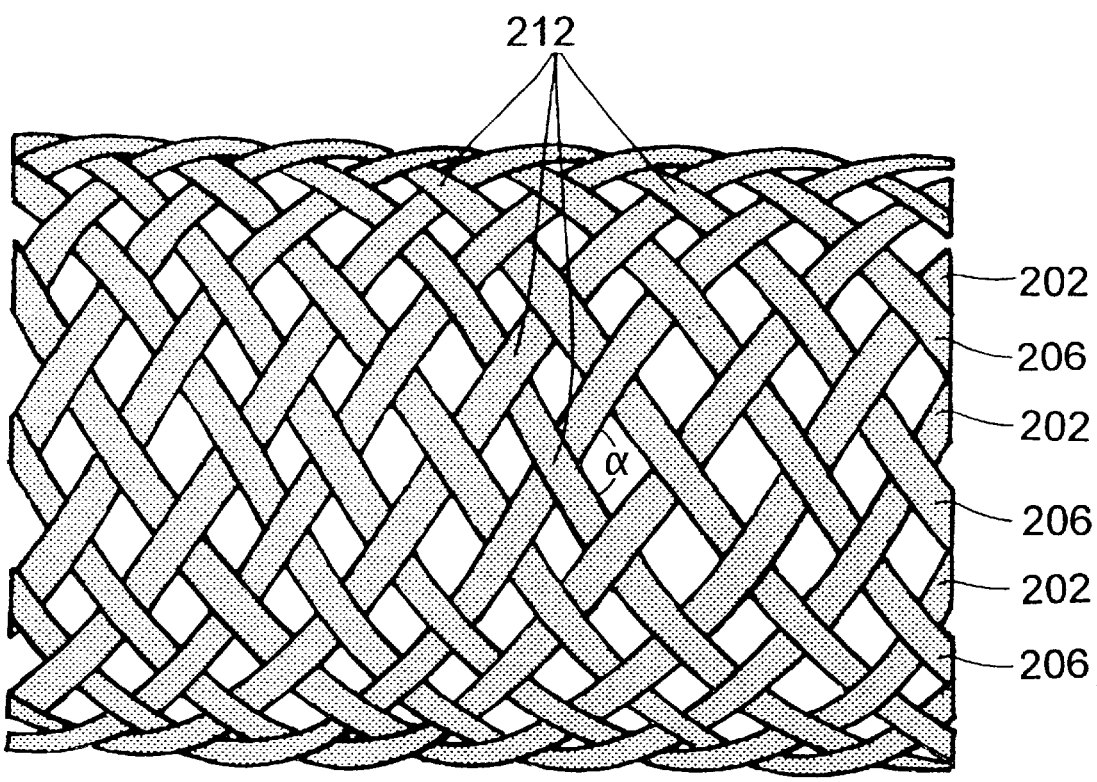
FIG. 6 is a plan view of a braided, self expanding stent in accordance with a fifth embodiment of the present invention.

In another embodiment of the invention, illustrated in FIG. 6, the axial filaments and/or axial bands of adhesive are omitted and the stent is either sprayed with or dipped in an adhesive solution. The enhanced radial self expansion force then is provided solely by the adhesive coating on the threads 202, 206 forming the body of the stent.

Figure 7:
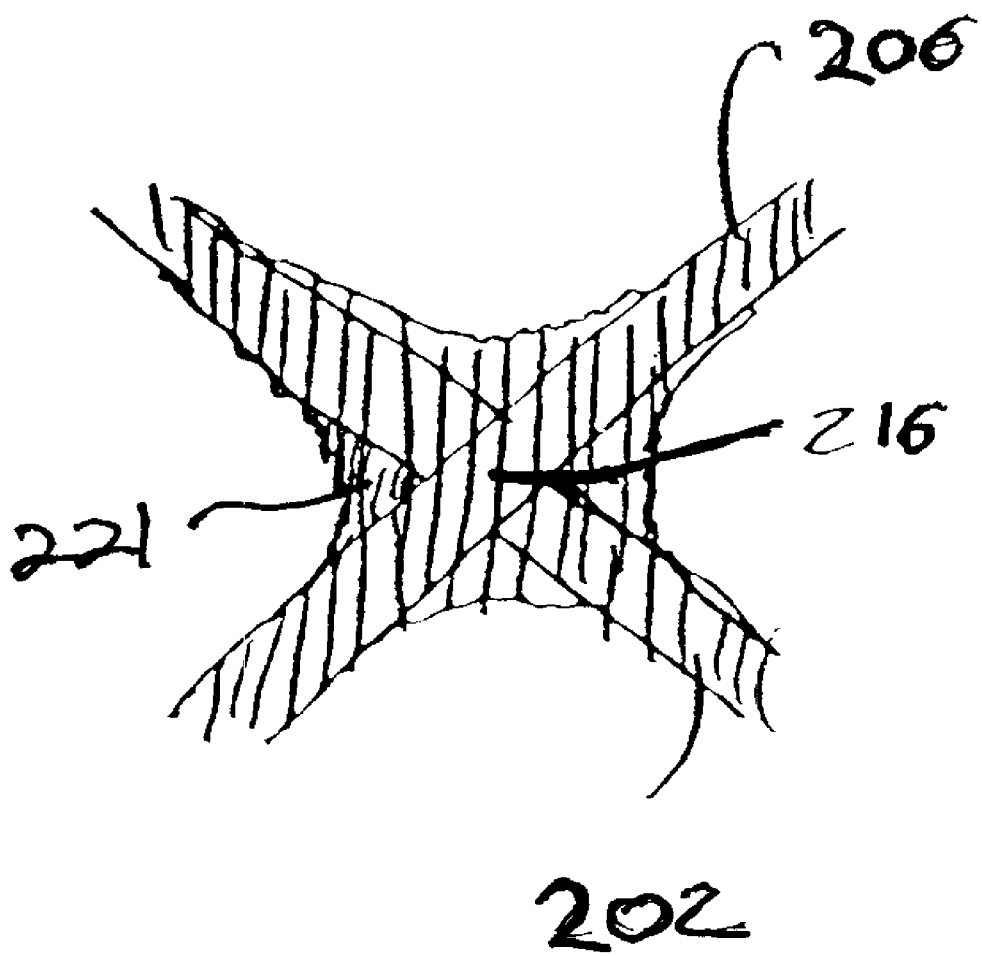
FIG. 7 is a close up view of a crossing point between two threads forming the body of a braided self-expanding stent in accordance with certain embodiments of the invention.

FIG. 7 is a close up view of a crossing point of two counter helically would threads forming part of the main body of a braided stent in which the stent has been sprayed with or dipped in adhesive in accordance with the embodiment of FIG. 6. FIG. 7, however, is also representative of the embodiment of FIG. 4. As can be seen in FIG. 7, webs of adhesive 221 form at the crossing points (or interstices) 216 where two counter helically wound threads 202 and 206 meet. The enhanced radial expansion force is provided particularly, but not necessarily solely, due to the formation of the webs 221 of adhesive at the interstices 216 of the counter helically wound threads 202 and 206 forming the main body of the stent.

While FIG. 6 illustrate a particular embodiment in which the entire stent body is covered with the adhesive, in other embodiments, only a portion of the stent may be covered with adhesive. For instance, depending on the particular embodiment, it may be desirable to dip only one or both ends of the stent in the adhesive. For example, if both ends of the stent were dipped in the glue, but the middle was left uncovered, then the stent would be stiffer near the ends than in the middle.

Those skilled in the art also will recognize that a stent in accordance with the present invention is an ideal vector for delivery of a drug or other medical substance. Such delivery could be accomplished by incorporating the drug or other substance into any part of the stent (threads, axial filament or adhesive) or coating any part of the stent with a drug eluding coating.

Those of skill in the relevant arts also will recognize that any part of the stent or entire stent can be made radiopaque by the addition a radiopaque filler such as a ceramic, metal, or metallic alloy powder.

EXAMPLE

A stent in accordance with the present invention was manufactured with 24 braided threads of a diameter of 0.27 mm. The threads were made of a copolymer of 96% poly-L-lactic acid and 4% poly-D-lactic acid. This copolymer was mixed with 20% by weight of $BaSO_4$ filler to improve its radiopacity. Four elastomeric filaments of Tecoflex 80-A having a diameter of approximately 0.25 mm each were interwoven into the stent body at the time of braiding. The axial filaments were adhered to the stent by applying an adhesive of Tecoflex 80-A dissolved in methylene chloride.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

We claim:

1. A method of fabricating a self-expanding stent with enhanced radial expansion force, said method comprising the steps of:

(1) providing a stent body in the shape of a tube;

(2) providing at least one filament arranged axially to said stent, said filament being elastic;

(3) attaching said filament to said stent body with an adhesive in a position such that said filament exerts an axial compression force on said stent body when said stent is axially elongated.

2. The method of claim 1 wherein said filament is positioned such that said filament exerts an axial compression force on said stent body when said stent is at a diameter that would otherwise be its rest diameter.

3. The method of claim 1 wherein said stent body is comprised of at least one thread and wherein step (3) comprises:

(3.1) placing said filament axially on said stent body (3.2) applying adhesive dissolved in a solvent to said filament; and (3.3) thereafter evaporating said solvent.

4. The method of claim 3 wherein step (3.2) comprises applying said adhesive in a band over the entire length of said filament.

5. The method of claim 3 wherein said stent body comprises a first set of threads helically wound in a first direction and a second set of threads helically wound in a second direction wherein said first set of threads and said second set of threads cross each other and wherein step (3.2) comprises applying said adhesive only at points where said axial filament intersects with said threads forming said stent body.

6. The method of claim 5 wherein step (3.1) comprises interweaving said filament with said threads forming said stent body.

7. The method of claim 3 wherein step (3.3) comprises heat treating said stents.

8. The method of claim 7 wherein said adhesive is a bioabsorbable polymer and said solvent is methylene chloride.

9. The method of claim 7 wherein said adhesive is silicone.

10. The method of claim 3 wherein step (3.1) comprises placing said filament on an outer surface of said stent body.

11. The method of claim 3 wherein step (3.1) comprises placing said filament on an inner surface of said stent body.

12. The method of claim 3 wherein said threads of said stent body are formed of a bioabsorbable polymer.

13. The method of claim 12 wherein said axial filaments are formed of a bioabsorbable polymer.

14. The method of claim 3 wherein said axial filaments are formed of a bioabsorbable polymer.

15. The method of claim 3 wherein said adhesive comprises a bioabsorbable polymer.

16. The method of claim 15 wherein said adhesive and said filaments are formed of the same material.

17. The method of claim 3 wherein said adhesive is silicone.

18. The method of claim 1 wherein step (3) comprises:
   (3.1) applying adhesive to said filament;
   (3.2) placing said filament with said adhesive axially on said stent body; and
   (3.3) thereafter heat treating said stent.

19. The method of claim 18 wherein step (3.2) comprises dipping said filament in a solution of said adhesive.

20. The method of claim 18 wherein step (3.2) comprises spraying said adhesive on said filament.

21. The method of claim 1 wherein step (3) comprises
   (3.1) placing said filament axially on said stent body
   (3.2) spraying adhesive dissolved in a solvent on said stent; and
   (3.3) thereafter evaporating said solvent.

22. The method of claim 1 wherein step (3) comprises
   (3.1) placing said filament axially on said stent body
   (3.2) dipping said stent in a solution of adhesive dissolved in solvent; and
   (3.3) thereafter evaporating said solvent.

23. A method of fabricating a self-expanding stent with enhanced radial expansion force, said method comprising the steps of:
   (1) providing a self-expanding stent body in the shape of a tube, said stent body formed of a plurality of intersection threads;
   (2) covering at least a portion of said stent body with an adhesive dissolved in a solvent; and
   (3) heat treating said stent to evaporate said solvent; whereby said threads are stiffened.

24. The method of claim 23 wherein step (2) comprises spraying said stent body with said adhesive dissolved in solvent.

25. The method of claim 23 wherein step (2) comprises dipping said stent body in said adhesive dissolved in solvent.

26. The method of claim 25 wherein said stent body comprises a first end section, a middle section, and a second end section arranged longitudinally along said stent body and wherein step (2) comprises:
   (2.1) dipping said first end section in said adhesive dissolved in solvent;
   (2.2) dipping said second end section in said adhesive dissolved in solvent.

27. A method of fabricating a self-expanding stent with enhanced radial expansion force, said method comprising the steps of:
   (1) providing a stent body in the shape of a tube; and
   (2) applying axial strips of adhesive to said stent body.

28. The method of claim 27 wherein said adhesive is elastomeric.

29. The method of claim 27 wherein step (2) comprises the steps of:
   (2.1) applying a solution comprising an adhesive dissolved in a solvent in axial strips on said stent body; and
   (2.2) evaporating said solvent.

30. The method of claim 29 wherein step (2.2) comprises heat treating said stent.

31. The method of claim 29 wherein step (2.1) comprises applying said solution with a syringe.

32. The method of claim 27 further comprising the step of:
   (3) prior to step (2), radially expanding said stent body to a position in which it has a radial diameter greater than its rest radial diameter and holding said stent in said position until said adhesive has bonded to said stent body.

33. The method of claim 27 wherein said adhesive is formed of a bioabsorbable polymer.

34. The method of claim 33 wherein said stent body is formed of a bioabsorbable polymer.

35. A self-expanding stent with enhanced radial expansion force comprising:
   a stent body in the shape of a tube; and
   at least one strip of adhesive running axially of said stent body and bonded to said stent body.

36. The stent of claim 35 wherein said adhesive is an elastomeric polymer.

37. The stent of claim 35 wherein, in the absence of an external force on said stent, said adhesive holds said stent body in a position in which it has a radial diameter greater than a resting radial diameter of said stent body.

38. The stent of claim 37 wherein said adhesive is formed of a bioabsorbable polymer.

39. The stent of claim 38 wherein said stent body is formed of a bioabsorbable polymer.

* * * * *